US006228841B1

(12) United States Patent
Sakurada et al.

(10) Patent No.: US 6,228,841 B1
(45) Date of Patent: May 8, 2001

(54) PEPTIDE DERIVATIVES

(75) Inventors: Shinobu Sakurada, Miyagi; Toru Okayama, Toyama; Eriko Nukui, Toyama; Kazuya Hongo, Toyama; Tadashi Ogawa, Toyama; Tomoko Hongo, Toyama; Satoko Takeshima, Toyama; Nobuhiro Take, Toyama; Masaharu Nakano, Toyama, all of (JP)

(73) Assignees: Daiichi Pharmaceutical Co., Ltd., Tokyo; Fuji Chemical Industries, Ltd., Toyama, both of (JP)

( * ) Notice: Subject to any disclaimer, the term of this patent is extended or adjusted under 35 U.S.C. 154(b) by 0 days.

(21) Appl. No.: 09/029,604

(22) PCT Filed: Sep. 10, 1996

(86) PCT No.: PCT/JP96/02572

§ 371 Date: Apr. 28, 1998

§ 102(e) Date: Apr. 28, 1998

(87) PCT Pub. No.: WO97/10261

PCT Pub. Date: Mar. 20, 1997

(30) Foreign Application Priority Data

Sep. 11, 1995 (JP) .................................... 7-232161

(51) Int. Cl.⁷ .................................... A61K 38/07
(52) U.S. Cl. .................................... 514/18; 530/330
(58) Field of Search .................................... 530/330, 331; 514/18

(56) References Cited

FOREIGN PATENT DOCUMENTS

| 61-36298 | 2/1986 | (JP) . |
| 95/24421 | 9/1995 | (WO) . |
| 96/2267 | 2/1996 | (WO) . |

OTHER PUBLICATIONS

Spatola, A. In: Chemistry and Biochemistry of Amino Acids, Peptides, and Proteins. B. Weinstein, Ed., N.Y., 1983,chapter 5.*
Hirioki Fujita et al., "Studies on Analgesic Oligopeptides. VI Further Studies of Synthesis and Biological Properties of Tripeptide Alkylamides, Tyr–D–Arg–Phe–X," *Chem. Pharm. Bull.* vol. 38, No. 8, 1990, pp. 2197–2200.
Journal of the American Chemical Society, vol. 95, pp. 1328–1333 (1973).
Sasaki et al. *Neuropeptides,* vol. 5, No. 4–6, pp. 391–394 (1985).
Sasaki et al. *Chem. Pharm. Bull.*, vol. 33, No. 4, pp. 1528–1536 (1985).
Suzuki et al. *Chem. Pharm. Bull.*, vol. 36, No. 12, pp. 4834–4840 (1988).
Sasaki et al. Chem. Pharm. Bull., vol. 39, No. 9, pp. 2316–2318 (1991).
An English language abstract of JP 61–36298.

\* cited by examiner

*Primary Examiner*—Michael Borin
(74) *Attorney, Agent, or Firm*—Greenblum and Bernstein, P.L.C.

(57) ABSTRACT

Compounds represented by the following general formula and salts thereof; Y-L-Tyr-Q-NR$^1$—CH(R$^2$)—CO—X, wherein R$^1$ represents hydrogen or $C_{1-6}$ alkyl; R$^2$ represents optionally substituted benzyl; Q represents D- or L-Arg; Y represents two hydrogen atoms of N-terminal amino group of L-Tyr, or one or two functional groups substituting for the hydrogen atoms, for example, a $C_{1-6}$ alkyl optionally having amino or carboxy; and X represents N-methyl-β-alanine and other. The compounds have analgesic effect and can be used for the treatment of cancer pain or the like.

5 Claims, No Drawings

PEPTIDE DERIVATIVES

TECHNICAL FIELD

The present invention relates to peptide derivatives exhibiting pharmaceutical activities such as analgesic activity through action on opioid receptors and the like.

BACKGROUND ART

The existence of opioid receptors to which opioids such as morphine bind was verified in the early 1970's. At present, opioid receptors are mainly classified into three types, i.e., $\mu$, $\delta$ and $\kappa$. Morphine mostly acts on the $\mu$ acceptor as an agonist and exhibits pharmaceutical activities such as analgesic activity, enterokinetic inhibition, and respiratory inhibition.

Since 1975, several endogenous morphine-like substances that bind to the opioid receptors have been successively discovered. All of these substances found to date are peptide compounds and are collectively referred to as opioid peptides. The pharmaceutical activities of the opioid peptides are believed to be basically the same as those of morphine. They are expected to be potentially safer drugs than morphine since they are substances naturally exist in living bodies. However, natural opioid peptides have problems from the pharmacokinetical standpoint, and they have not been used as clinical medicaments.

In the 1980's, Delmorphine that contains D-alanine was isolated from cutises of frogs. It was found that Delmorfine has about 1000-fold higher analgesic effect than morphine at intraventricular administration and is relatively stable in living bodies. Since then, synthetic opioid peptides containing D-amino acids have been prepared. In particular, synthetic opioid peptides with high $\kappa$ acceptor selectivity are considered as hopeful non-narcotic analgesics and clinical trials have begun. However, the probability of their success as clinical medicaments is doubtful from the viewpoints of efficacy, possible side effects probably due to properties as $\kappa$ agonists, and commercial practicability.

Furthermore, it is impossible to use these synthesized opioid peptides as orally available medicaments, and accordingly, they can not be substitutive drugs for MS contin, e.g., which is an orally available controlled release preparation comprising morphine sulfate that has been widely used recently as a medicament for treatment of cancerous pain. However, daily dose of MS contin may occasionally be increased up to gram order, which sometimes leads to difficulty in oral administration. In some cases, its administration cannot be continued because of side effects such as pruritus due to its activity on the release of histamine. Therefore, substitutive medicaments are desired which have higher safety and efficacy than morphine.

DISCLOSURE OF THE INVENTION

In order to achieve the aforementioned objects, the inventors of the present invention conducted various studies aimed at providing opioid peptide derivatives having excellent analgesic activity and oral absorbability. As a result, they found that oligopeptide derivatives and their salts having a basic structure of L-Tyr-(L or D)-Arg-Phe and an amidino group at the N-terminal have the desired properties, and filed patent applications pertaining to these peptide derivatives (Japanese Patent Applications Nos. (Hei) 6-40989/1994 and (Hei) 7-49894/1995). The inventors conducted further studies and found that the aforementioned peptide derivatives modified at the amidino group at the N-terminal have the desired properties. The present invention was achieved on the basis of these findings.

That is, the peptide derivatives of the present invention are represented by the following Formula I:

Y-L-Tyr-Q-NR¹—CH(CH₂C₆H₅)—CO—X.

According to the present invention, a medicament consisting of said compound or a salt thereof, and a analgesic pharmaceutical composition comprising said compound or a salt thereof as an active ingredient are provided. Use of said compound or a salt thereof for manufacture of the aforementioned pharmaceutical composition; and method for preventive and/or therapeutic treatment of pain comprising a step of administering to an mammal an effective amount of said compound or a salt thereof are also provided according to the present invention.

BEST MODE FOR CARRYING OUT THE INVENTION

As for the substituents in the above formula, Q represents D-Arg (D-arginine residue) or L-Arg (L-arginine residue), and $R^1$ represents hydrogen atom or a $C_{1-6}$ (having 1–6 carbon atoms) alkyl group. Among them, those compounds where Q is D-Arg and $R^1$ is hydrogen atom are preferred. The term $C_{1-6}$ alkyl referred to in the present specification is used to embrace a linear alkyl group, a branched alkyl group, a cyclic alkyl group, and a linear or branched alkyl group substituted with a cyclic alkyl group. As the $C_{1-6}$ alkyl group, for example, methyl group, ethyl group, n-propyl group, isopropyl group, cyclopropyl group, n-butyl group, sec-butyl group, tert-butyl group, cyclopropylmethyl group, cyclobutyl group and the like may preferably be used.

$R^2$ represents a benzyl group which may optionally be substituted. When the benzyl group is substituted, it may have one or more substituents at any substitutable positions. When it has two or more substituents, they may be the same or different. As substituents on the phenyl ring, for example, a $C_{1-6}$ alkyl group, an amino group which may optionally be substituted, a guanidino group which may optionally be substituted, hydroxyl group and the like may be used. Among them, unsubstituted benzyl group is preferred.

Y represents two hydrogen atoms of N-terminal amino group of L-Tyr, or one or two functional groups substituting for one or two of the hydrogen atoms. The functional group is selected from the group consisting of: a $C_{1-6}$ alkyl group which may have an amino group, a $C_{1-6}$ alkyl group which may have a carboxyl group, a $C_{1-6}$ alkylcarbonyl group which may have an amino group, a sulfonyl group which may have an alkyl group, a pyrimidyl group which may optionally be substituted, an imidazolinyl group which may optionally be substituted, and a group represented by the following formula: $HN=C(R^3)-$ (wherein $R^3$ represents hydrogen atom, a $C_{1-6}$ alkyl group, a phenyl group which may optionally be substituted, a hydroxyamino group which may optionally be substituted, or a hydrazino group which may optionally be substituted). When the two hydrogen atoms are replaced by the above functional groups, each of the functional groups is independently selected from the above group, and may be the same or different to each other.

Methyl group, ethyl group, isopropyl group, cyclopropylmethyl group and the like are preferred as the $C_{1-6}$ alkyl group represented by Y. When the $C_{1-6}$ alkyl group represented by Y has amino group or carboxyl group, examples include the groups of $H_2N-CH_2-$, $H_2N-(CH_2)_2-$, $HOOC-CH_2-$, $HOOC-(CH_2)_2-$ and the like. When the $C_{1-6}$ alkylcarbonyl group has amino group, examples include $H_2N-CH_2-CO-$, $H_2N-(CH_2)_2-CO-$ and the like. An example of a sulfonyl group having a $C_{1-6}$ alkyl group is, for example, the group of $CH_3SO_2-$.

2-Pyrimidyl group and 2-imidazolin-2-yl group and the like can be preferably used as the pyrimidyl group and the imidazolinyl group represented by Y, respectively. The pyrimidyl group and the imidazolinyl group may be either substituted or unsubstituted. When the pyrimidyl group or the imidazolinyl group is substituted, a $C_{1-6}$ alkyl group and the like may be used as the substituent, and when these groups have two or more substituents, they may be the same or different. An example of the substituted pyrimidyl group includes 4,6-dimethyl-2-pyrimidyl group, and an example of the substituted imidazolinyl group includes 4-methyl-2-imidazolin-2-yl group.

$R^3$ represents hydrogen atom, a $C_{1-6}$ alkyl group, a phenyl group which may optionally be substituted, a hydroxyamino group which may optionally be substituted, or a hydrazino group which may optionally be substituted. Methyl group, ethyl group, n-propyl group and the like are preferred as the $C_{1-6}$ alkyl group represented by $R^3$, and methyl group is particularly preferred. As for the phenyl group, the hydroxyamino group (HO—NH—) and the hydrazino group ($H_2N$—NH—), those unsubstituted may preferably be used, however, those substituted with one or more $C_{1-6}$ alkyl groups may also be used.

It is preferred that Y represents two hydrogen atoms, or one of Y is a hydrogen atom and the other is the aforementioned functional group. It is also preferred that both of Y are two functional groups mentioned above, for example, the same or different $C_{1-6}$ alkyl groups. Preferred embodiments of the present invention include the compounds where the two substituents represented by Y are methyl groups.

X represents either of $-OR^4$, $-N(R^5)(R^6)$ or $-NR^7-C(R^8)(R^9)(R^{10})$. $R^4$ represents hydrogen atom or a $C_{1-6}$ alkyl group, and $R^5$ represents hydrogen atom or a $C_{1-6}$ alkyl group. $R^6$ represents a $C_{1-6}$ hydroxyalkyl group or a sulfonic acid-substituted $C_{1-6}$ alkyl group. The hydroxy group or the sulfonic acid group may be at any substitutable position of an alkyl group, however, an alkyl group substituted at its terminal is preferred. $R^5$ and $R^6$ may combine to form a 5- or 6-membered nitrogen-containing saturated heterocyclic group together with the nitrogen atom to which $R^5$ and $R^6$ bind, and the heterocyclic ring may contain two or more nitrogen atoms. For example, 1-piperazinyl group, 1-pyrrolidinyl group, 1-piperidinyl group or the like may be used as $-N(R^5)(R^6)$.

When X represents $NR^7-C(R^8)(R^9)(R^{10})$, $R^7$ represents hydrogen atom, a $C_{1-6}$ alkyl group, or a $C_{1-6}$ alkyl group substituted with an aryl group such as phenyl group (aralkyl group). An example of the aralkyl group includes benzyl group. $R^8$ represents hydrogen atom; carboxyl group; a carbonyl group substituted with a $C_{1-6}$ alkoxyl group such as methoxycarbonyl and ethoxycarbonyl; a substituted or unsubstituted carbamoyl group; a $C_{1-6}$ alkyl group substituted with a carboxyl group; a $C_{1-6}$ alkyl group substituted with a substituted or unsubstituted carbamoyl group; or a $C_{1-6}$ alkyl group having a carbonyl group substituted with a $C_{1-6}$, alkoxyl group.

$R^9$ represents hydrogen atom; a $C_{1-6}$ alkyl group; an amino-$C_{1-6}$ alkyl group; a $C_{1-6}$ alkyl group substituted with an amidino group; a $C_{1-6}$ alkyl group substituted with a guanidino group; a hydroxy-$C_{1-6}$ alkyl group; a Clan alkyl group substituted with a carboxyl group; or a $C_{1-6}$ alkyl group substituted with a substituted or unsubstituted carbamoyl. Alternatively, $R^7$ and $R^9$ may combine to form a 5- or 6-membered nitrogen-containing saturated heterocyclic group having a carboxyl group on the ring together with the nitrogen atom to which $R^7$ binds. Examples of the heterocyclic ring include 2-carboxy-1-pyrrolidinyl group (-Pro-OH), 3-carboxy-1-piperidinyl group and the like. Among them, for example, combinations where $R^8$ is carboxymethyl group or carbamoylmethyl group and $R^9$ is hydrogen atom are preferred. $R^{10}$ represents hydrogen atom or a $C_{1-6}$ alkyl group. In each of the substituents mentioned above, alkyl groups, alkoxyl groups and alkanoyl groups may be either linear or branched.

The compounds of the present invention represented by Formula I mentioned above contain, in addition to the two asymmetric carbons derived from the L-tyrosine residue and the D-Arg or L-Arg residue represented by Q, an asymmetric carbon atom derived from a phenylalanine residue binding to Q, an asymmetric carbon atom to which $R^8$ and $R^9$ bind (except for compounds where $R^8$ and $R^9$ simultaneously represent identical substituents), and one or more asymmetric carbon atoms which may exist in the aforementioned substituents and Y. The asymmetric carbon atoms other than those derived from L-Tyr, D-Arg and L-Arg residues may be either in R- or S-configuration. Any optically active isomers, racemates, diastereoisomers of the compounds represented by the formula, and any mixtures of such isomers fall within the scope of the compounds of the present invention represented by Formula I.

Acid addition salts such as hydrochlorides, acetates, or p-toluenesulfonates, or base addition salts such as ammonium salts or organic amine salts fall within the scope of the compounds of the present invention. In addition to the compounds represented by the above general formula, dimers or oligomers derived from the above compounds and cyclic compounds produced by binding C-terminals and N-terminals of these compounds also fall within the scope of the compounds of the present invention.

The peptides of the present invention have higher analgesic activity than morphine. Since their analgesic activity is accompanied by relatively weaker effects on the release of histamine and heart rate depression than those of morphine, and since their degree of cross resistance between morphine is low, they can be expected to be suitable for the treatment of cancerous pain. Therefore, according to the present invention, there are provided pharmaceutical compositions comprising the above compounds. Examples of the route of administration include, for example, intravenous administration, subcutaneous administration, and oral administration. Formulations for mucosal absorption including nasal absorption and formulations for endermic absorption are also expected to be useful. Dose of administration is not particularly limited. For example, a single dose of 0.1 to 10 mg for subcutaneous administration, or a single dose of 1 to 100 mg for oral administration may be administered twice or three times a day.

The peptide derivatives of the present invention can be prepared by a solid phase method or a liquid phase method ordinarily used for peptide preparations. Various excellent agents are available as protective groups for amino groups and the like and as condensing agents and the like for condensation reactions. These can be suitably selected with reference to Examples set out below, or in view of, for example, Koichi Suzuki Ed., "Tanpakushitu Kohgaku-Kiso to Ohyo (Protein Engineering: Fundamentals and Applications)," Maruzen Co., Ltd. (1992) and publications cited therein; M. Bondanszky, et al., "Peptide Synthesis," John Wiley & Sons, New York, 1976; and J. M. Stewart and D. J. Young, "Solid Phase Peptide Synthesis," W. H. Freeman and Co., San Francisco, 1969. For the solid phase methods, various commercially available peptide synthesizers, for example, Model 430A (Perkin Elmer Japan, formerly Applied Biosystems), may conveniently be used. Resins, reagents and the like used in the syntheses are easily obtainable as commercially available products and examples are indicated in Examples.

EXAMPLES

The present invention will be explained more specifically by examples. However, the present invention is not limited to the examples. By referring to the examples, modifying or altering the methods of the examples, or appropriately selecting starting materials or reagents for reactions, desired peptide derivatives of the present invention that fall within the scope of the general Formula I can easily be prepared. In the examples, the meanings of amino acid groups are similar to those ordinarily used. Where an amino acid having D-form or L-form is referred to, the amino acid represents an L-amino acid unless specifically described as D-form. In addition, the following abbreviations will be used, and similar abbreviations not specifically defined below will also be used.

Z: benzyloxycarbonyl group,
OTce: trichloroethyl ester group,
Boc: t-butoxycarbonyl group,
WSCI: 1-ethyl-3-(3-dimethylaminopropyl)carbodiimide,
TosOH: p-toluenesulfonic acid,
OBzl: benzyloxy group,
Me β Ala or β MeAla: N-methyl-β-alanine,
H-β Ala-ol: $NH_2CH_2CH_2CH_2OH$,
Fmoc: 9-fluorenylmethyloxycarbonyl,
Pmc: 2,2,5,7,8-pentamethylchroman-6-sulfonyl,
t-Bu: tertiary butyl,
NMP: N-methylpyrrolidone,
DMF: dimethylformamide,
DMSO: dimethyl sulfoxide,
TFA: trifluoroacetic acid,
TEA: triethylamine,
DCM: dichloromethane,
DMAP: N,N-dimethylaminopyridine,
DIPEA: N,N-diisopropylethylamine,
DIPCI: N,N-diisopropylcarbodiimide,
HOBt: 1-hydroxybenzotriazole,
EDC: 1-(3-dimethylaminopropyl)-3-ethylcarbodiimide,
HBTU: 2-(1H-benzotriazole-1-yl)-1,1,3,3-tetramethyluronium hexafluorophosphate,
PyBrop: Bromotris(pyrrolidino)phosphonium hexafluorophosphate,
Alko resin : p-alkoxybenzyl alcohol resin [4-hydroxymethylphenoxymethyl-co-polystyrene, 1% divinylbenzene resin, J. Am. Chem. Soc., 95, 1328 (1973), Watanabe Chemical Industry],
Fmoc-NH-SAL resin: 4-(2',4'-dimethoxyphenyl-9-fluorenylmethoxycarbonylamino-methyl)phenoxy resin (Watanabe Chemical Industry).

In the Examples set out below, the conditions of thin layer chromatography were as follows:

$Rf^a$: N-butanol: acetic acid: purified water=4:1:5 were mixed, and the upper layer was used as a developing solvent.

$Rf^b$: N-butanol: acetic acid: purified water: pyridine= 15:3:10:12 was used as a developing solvent.

Thin layer plate: silica gel (Merck F254)
(A) Preparation of a Starting Material
(1) H-Tyr-D-Arg-Phe-β-Ala-OH The above peptide was prepared by the solid phase method (Original Autoprogram for the Fmoc/NMP method) using a Model 430A peptide synthesizer (Applied Biosystems, ABI) as follows. Fmoc-β Ala-Alko resin (0.25 mmol, 675 mg) was washed once with NMP and treated with NMP containing 20% piperidine for 4 minutes, and then with NMP containing 20% piperidine for 16 minutes. The resin was washed with NMP five times, and then allowed to react with Fmoc-Phe-OH for 61 minutes. Then, the resin was washed with NMP four times and recovered from the fourth rinse, and unreacted amino groups were allowed to react with acetic anhydride. The above-described first cycle was carried out in 120 minutes, and similar procedure was repeated using Fmoc-D-Arg(Pmc)-OH for the second cycle, and Fmoc-Tyr(t-Bu)-OH for the third cycle in place of Fmoc-Phe-OH. As side chain protective groups, Pmc was used for D-Arg, and t-Bu for Tyr.

The resin obtained in the above procedure (500 mg) was treated with stirring in a mixture of phenol (crystal, 0.75 g), ethanedithiol (0.25 ml), thioanisole (0.50 ml), water (0.50 ml), and TFA (10.0 ml) at room temperature for 3 hours to liberate peptides from the resin and simultaneously remove the protective groups. Then, the mixture was filtered using a 3 μm filter (ADVANTEC-Polyflon filter), cold diethyl ether (200 ml) was added to the filtrate, and the resulting precipitates were collected by filtration using a 3 μm filter (ADVANTEC-Polyflon filter). The precipitates on the filter were dissolved in 10 to 20 ml of 2N acetic acid and lyophilized to give crude peptide of the formula H-Tyr-D-Arg-Phe-β-Ala-OH.

(2) H-Tyr-D-Arg-Phe-$NHCH_2CH_2CONH_2$

The above peptide was obtained in the same manner as in the above (1) except that Fmoc-NH-SAL resin (0.25 mmol, 385 mg) was used at the beginning of the synthesis.

(3) H-Tyr-D-Arg-Phe-β-MeAla-OH

The above peptide was prepared by the solid phase method (Fmoc/NMP method) as follows. A glass filter was used for filtration. After Alko resin (0.500 g) had been swollen with DMF (6 ml), the resin was added with Fmoc-N-methyl-β-alanine (Fmoc-β-MeAla-OH, 0.228 g) and pyridine (0.093 ml), shaken for 1 minute, and then added with 2,6-dichlorobenzoyl chloride (0.147 g) and shaken for 24 hours. The resulting Fmoc-βMeAla-Alko resin was washed three times with 6 ml of DMF, then three times with 6 ml of methanol and further three times with 6 ml of DCM, and unreacted hydroxymethyl groups were benzoylated by adding benzoyl chloride (0.0891 ml) and pyridine (0.0847 ml) in DCM (6 ml) and shaking for 1 hour. The amino acid resin was successively washed three times with 6 ml of DCM, three times with 6 ml of DMF and three times with 6 ml of methanol and dried in vacuum in a desiccator over potassium hydroxide.

The Fmoc-β-MeAla-Alko resin was treated three times with 12 ml of DMF, then three times with 12 ml of DMF containing 20% piperidine and further six times with 12 ml of DMF to remove the Fmoc group, then added with Fmoc-Phe-OH (0.262 g), PyBrop (Watanabe Chemical Industry, 0.315 g), NMP (6 ml) and DIPEA (0.273 ml) and shaken for 24 hours to form Fmoc-Phe-β-MeAla-Alko resin. After filtration and washing with 6 ml of NMP, unreacted amino groups were capped by treatment with DMF (6 ml) containing 1-acetylimidazole (0.248 g) and DIPEA (0.0784 ml) for 1 hour. The resulting resin was then washed with 6 ml of NMP.

The Fmoc group was removed from the Fmoc-Phe-β-MeAla-Alko resin obtained in the same manner as described above, and the resultant was added with Fmoc-D-Arg(Pmc)-

OH (0.557 g), HOBt (0.121 g), HBTU (0.299 g) and DIPEA (0.274 ml) and shaken for 1 hour to form Fmoc-D-Arg (Pmc)-Phe-β-MeAla-Alko resin. After filtration and washing, unreacted amino groups were capped in the same manner as described above.

The Fmoc group was removed from the Fmoc-D-Arg (Pmc)-Phe-βMeAla-Alko resin in the same manner as described above, and the resultant was added with Fmoc-Tyr(t-Bu)-OH (0.310 g), HOBt (0.103 g), HBTU (0.256 g) and DIPEA (0.235 ml) and shaken for 1 hour to form Fmoc-Tyr(t-Bu)-D-Arg(Pmc)-Phe-β-MeAla-Alko resin. After filtration and washing, unreacted amino groups were capped in the same manner as described above. The peptide was liberated from the resin and the protective group was simultaneously removed in the same manner as in the above (1).

(4) H-Tyr-D-Arg-Phe-β-EtAla-OH

The above peptide was prepared by the solid phase method (Fmoc/NMP method) as follows. A glass filter was used for filtration. After Alko resin (1.000 g) had been swollen with NMP (12 ml), the resin was added with Fmoc-N-ethyl-β-alanine (Fmoc-βEtAla-OH, 0.475 g) and DMAP (0.017 g), shaken for 1 minute, then added with DIPCI (0.177 g) and shaken for 24 hours. The resulting Fmoc-β-EtAla-Alko resin was washed three times with 12 ml of NMP, then three times with 12 ml of methanol, and further three times with 12 ml of DCM, and unreacted hydroxymethyl groups were benzoylated by adding benzoyl chloride (0.178 ml) and pyridine (0.170 ml) in DCM (12 ml) and shaking 1 hour. The amino acid resin was successively washed three times with 12 ml of DCM, three times with 12 ml of DMF, and three times with 12 ml of methanol and dried in vacuum in a desiccator over potassium hydroxide.

The Fmoc-β-EtAla-Alko resin was treated three times with 20 ml of DMF, then three times with 12 ml of DMF containing 20% piperidine and further six times with 12 ml of DMF to remove the Fmoc group, then added with Fmoc-Phe-OH (0.387 g), PyBrop (0.466 g), NMP (12 ml) and DIPEA (0.523 ml), and shaken for 24 hours to form Fmoc-Phe-β-EtAla-Alko resin. After filtration and washing with 12 ml of NMP, unreacted amino groups were capped by treatment with DMF (12 ml) containing 1acetylimidazole (0.551 g) and DIPEA (0.174 ml) for 1 hour. The resulting resin was washed again with 12 ml of NMP.

The Fmoc group was removed from the Fmoc-Phe-β-EtAla-Alko resin in the same manner as described above. The resin was added with Fmoc-D-Arg(Pmc)-OH (0.707 g), HOBt (0.153 g), HBTU (0.379 g) and DIPEA (0.348 ml) and shaken for 1 hour to form Fmoc-D-Arg(Pmc)-Phe-β-EtAla-Alko resin. After filtration and washing, unreacted amino groups were capped in the same manner as described above.

The Fmoc group was removed from the Fmoc-D-Arg (Pmc)-Phe-β-EtAla-Alko resin obtained above in the same manner as described above, and the resultant was added with Fmoc-Tyr(t-Bu)-OH (0.460 g), HOBt (0.153 g), HBTU (0.399 g) and DIPEA (0.348 ml), and shaken for 1 hour to form Fmoc-Tyr(t-Bu)-D-Arg(Pmc)-Phe-β-EtAla-Alko resin. After filtration and washing, unreacted amino groups were capped in the same manner as described above. The peptide was separated from the resin, and the protective group was simultaneously removed in the same manner as in the above (1).

(5) H-Tyr(Bzl)-D-Arg($Z_2$)-Phe-OTce

The starting material, Z-Phe-OTce (254 g), was treated with 25% hydrogen bromide-acetic acid (900 ml) to remove Z group, and then dissolved in $CH_2Cl_2$ (1000 ml) on an ice bath. After this solution was added with Boc-D-Arg($Z_2$)-OH (288 g) and HOBt (85 g) and neutralized with TEA (77 ml), condensation reaction was carried out by using EDC.HCl (121 g) to form Boc-D-Arg($Z_2$)-Phe-OTce. Then, Boc-D-Arg($Z_2$)-Phe-OTce (241 g) was treated with 4N HCl/ethyl acetate (1,000 ml) to remove the Boc group, and dissolved in DMF (1,300 ml) on an ice bath. After the solution was added with Boc-Tyr(Bzl)-OH (108 g) and HOBt (46 g) and neutralized with TEA (42 ml), condensation reaction was carried out using EDC.HCl (65 g) to obtain a protected peptide of the following formula: Boc-Tyr(Bzl)-D-Arg($Z_2$)-Phe-OTce. The Boc-Tyr(Bzl)-D-Arg($Z_2$)-Phe-OTce. The Boc-Tyr(Bzl)-D-Arg($Z_2$)-Phe-OTce (48 g) was treated with 4N HCl/ethyl acetate (250 ml) to remove Boc group.

(6) H-Tyr(Bzl)-D-Arg($Z_2$)-MePhe-MeβAla-OBzl

Using TosOH.MegAla-OBzl as a starting material, the above peptide was prepared successively from the C-terminals by a liquid phase method. Boc-MePhe-OH and TosOH.MeβAla-OBzl were condensed by the EDC-HOBt method to obtain Boc-MePhe-MeβAla-OBzl. Boc group was removed from the Boc-MePhe-MeβAla-OBzl using 4N HCl/ethyl acetate, and the resultant was condensed with Boc-D-Arg($Z_2$)-OH by the EDC-HOBt method to form Boc-D-Arg($Z_2$)-MePhe-MeβAla-OBzl. Subsequently, Boc group was removed from the Boc-D-Arg($Z_2$)-MePhe-MeβAla-OBzl using 4N HCl/ethyl acetate, and the resultant was condensed with Boc-Tyr(Bzl)-OH by the EDC-HOBt method to obtain a protected peptide Boc-Tyr(Bzl)-D-Arg ($Z_2$)-MePhe-MeβAla-OBzl. Boc group was then removed by treating with 4N HCl/ethyl acetate (250 ml).

(B) Preparations of the Compounds of the Invention

EXAMPLE 1

N-Methyl-Tyr-D-Arg-Phe-MeβAla-OH.diacetate

Boc-Phe-OH and Tos.OH MeβAla-OBzl were condensed by the EDC-HOBt method to obtain Boc-Phe-MeβAla-Obzl. After Boc group was removed by using 4N HCl/ethyl acetate from the Boc-Phe-MeβAla-OBzl, the resulting product was condensed with Boc-D-Arg($Z_2$)-OH by the EDC-HOBt method to obtain Boc-D-Arg($Z_2$)-Phe-MeβAla-OBzl.

The Boc-D-Arg($Z_2$)-Phe-MeβAla-OBzl (4.76 g, 5.50 mmol) was dissolved in 4N-HCl/ethyl acetate solution (20 ml), and stirred at room temperature for 25 minutes. Diethyl ether was added to the reaction mixture, and the deposited crystals were collected by filtration. These crystals were dissolved in dimethylformamide (10 ml), and Boc-N-methyl-Tyr(Bzl)-OH (1.93 g, 5.00 mmol), 1-hydroxybenzotriazole (743 mg, 5.50 mmol) and triethylamine (0.84 ml, 6.0 mmol) were dissolved in the solution. This solution was cooled to −10° C., then added with 1-ethyl-3-(3-dimethylaminopropyl)-carbodiimide hydrochloride (1.15 g, 6.00 mmol), and stirred at −10° C. for one hour and at room temperature for 20 hours. The reaction mixture was added with ethyl acetate (40 ml), and washed with 1N HCl, and then with saturated aqueous sodium hydrogencarbonate. The solvent was concentrated under reduced pressure to obtain an oily product, which was purified by silica gel column chromatography (benzene: ethyl acetate=2:1 (v/v)) to obtain 5.01 g of Boc-N-methyl-Tyr(Bzl)-D-Arg($Z_2$)-Phe-MeβAla-OBzl as a colorless oily product.

This protected peptide (0.84 g, 0.74 mmol) was dissolved in 4N-HCl/ethyl acetate solution (5 ml), and stirred at room temperature for 30 minutes. Diethyl ether was added to the reaction mixture, and the deposited crystals were collected by filtration. These crystals were dissolved in acetic acid (5 ml), and added with 5% Pd-C (water content: 50%, 0.3 g) as catalyst, and catalytic reduction was carried out for three hours to remove the protective group. After the catalyst was removed by filtration, the reaction mixture was lyophilized to obtain 396 mg of the title compound as white powder.

FAB mass spectrum m/z: 584 (M+H$^+$); $[\alpha]_D^{23}$ +44.4° (c=1.01, 1N-acetic acid); Rf$^b$: 0.59.

EXAMPLE 2
N,N-Dimethyl-Tyr-D-Arg-Phe-MeβAla-OH.diacetate

Boc-D-Arg($Z_2$)-Phe-MegβAla-OBzl (1.30 g, 1.50 mmol) was dissolved in 4N-HCl/ethyl acetate solution (15 ml), and stirred at room temperature for 40 minutes. Diethyl ether was added to the reaction mixture, and the deposited crystals were collected by filtration. These crystals were dissolved in dimethylformamide (10 ml), and N,N-dimethyl-Tyr(Bzl)-OH (419 mg, 1.40 mmol), 1-hydroxybenzotriazole (189 mg, 1.40 mmol) and triethylamine (0.21 ml, 1.5 mmol) were dissolved in the solution. This solution was cooled to −10° C., then added with 1-ethyl-3-(3-dimethylaminopropyl)-carbodiimide hydrochloride (349 mg, 1.82 mmol), and stirred at −10° C. for one hour and then at room temperature for 20 hours. The reaction mixture was added with ethyl acetate (40 ml), and washed with 1NHCl, and then with saturated aqueous sodium hydrogencarbonate. The solvent was concentrated under reduced pressure to obtain an oily product, which was purified by silica gel column chromatography (benezene: ethyl acetate=2:1 (v/v)) to obtain 974 mg of N,N-dimethyl-Tyr(Bzl)-D-Arg($Z_2$)-Phe-MeβAla-OBzl as colorless amorphous solid.

This protected peptide (450 mg, 0.43 mmol) was dissolved in acetic acid (5 ml), and added with 5% Pd-C (water content: 50%, 0.29 g) as catalyst, and catalytic reduction was carried out for four hours to remove the protective group. After the catalyst was removed by filtration, the mixture was lyophilized to obtain 193 mg of the title compound as white powder.

FAB mass spectrum m/z: 598 (M+H$^+$); $[\alpha]_D^{23}$ +44.4° (c=1.08, 1N-acetic acid); Rf$^b$: 0.37

EXAMPLE 3
N-Ethyl-Tyr-D-Arg-Phe-MeβAla-OH.diacetate

Boc-Tyr(Bzl)-D-Arg($Z_2$)-Phe-MeβAla-OBzl (2.20 g, 2.00 mmol) was dissolved in 4N-HCl/ethyl acetate solution (10 ml), and stirred at room temperature for 1 hour. Diethyl ether was added to the reaction mixture, and the deposited crystals were collected by filtration. These crystals were dissolved in methanol (10 ml), and acetaldehyde (134 μl, 2.40 mmol) and sodium cyanoborohydride (132 mg, 2.00 mmol)) were dissolved in the solution with stirring under ice cooling. After stirred for 17 hours at room temperature, the solution was added with the same amounts of acetaldehyde and sodium cyanoborohydride, and further stirred at room temperature for 19 hours. The reaction mixture was concentrated under reduced pressure, added with chloroform (50 ml), and then washed with water. An oily product obtained by removing chloroform under reduced pressure was purified by silica gel column chromatography (benzene: ethyl acetate=1:3 (v/v)) to obtain 1.37 g of N-ethyl-Tyr(Bzl)-D-Arg($Z_2$)-Phe-MeβAla-OBzl as a colorless oily product.

This protected peptide (0.84 g, 0.74 mmol) was dissolved in acetic acid (5 ml), and added with 5% Pd-C (water content: 50%, 0.30 g) as catalyst, and catalytic reduction was carried out for three hours to remove the protective group. After the catalyst was removed by filtration, the mixture was lyophilized to obtain 396 mg of the title compound as white powder.

FAB mass spectrum m/z: 598 (M+H$^+$); $[\alpha]_D^{23}$ +42.1° (c=1.02, 1N-acetic acid); Rf$^b$: 0.53.

EXAMPLE 4
N-Isopropyl-Tyr-D-Arg-Phe-MeβAla-OH.diacetate

By using Boc-Tyr(Bzl)-D-Arg($Z_2$)-Phe-MeβAla-OBzl (2.00 g, 2.00 mmol), acetone (147 μl, 2.00 mmol) and sodium cyanoborohydride (138 mg, 2.00 mmol), 754 mg of the title compound was obtained as white powder as in Example 3.

FAB mass spectrum m/z: 612 (M+H$^+$); $[\alpha]_D^{23}$ +48.7° (c=1.02, 1N-acetic acid); Rf$^b$: 0.60.

EXAMPLE 5
N-Cyclopropylmethyl-Tyr-D-Arg-Phe-MeβAla-OH.diacetate (1) N-Cyclopropylmethyl-N-benzyloxycarbonyl-Tyr(Bzl)-OH H-Tyr(Bzl)-OMe hydrochloride (4.83 g, 15.0 mmol) and cyclopropylmethyl bromide (2.43 g, 18.0 mmol) were dissolved in dimethylformamide (20 ml), and then the solution was added with diisopropylethylamine (3.48 ml, 20.0 mmol) and stirred at room temperature for 24 hours. The reaction mixture was concentrated, and the residue was dissolved in ethyl acetate (100 ml) and then washed with 10% aqueous citric acid and saturated aqueous sodium hydrogencarbonate successively. The ethyl acetate was evaporated under reduced pressure, and the resulting crude product was purified by silica gel column chromatography (chloroform: methanol=50:1 (v/v)) to obtain 1.91 g of a colorless oily product.

This oily product was dissolved in methylene chloride (20 ml), and the solution was added with 10% aqueous sodium carbonate and benzyloxycarbonyl chloride (1.03 ml, 7.28 mmol) and then vigorously stirred at room temperature for 22 hours. The methylene chloride layer was concentrated, and the resulting crude product was dissolved in methanol (5.7 ml), and the solutinon was added with 2N aqueous sodium hydroxide (5.7 ml) and then stirred at room temperature for 18 hours. After the solvent was evaporated under reduced pressure, the mixture was adjusted to about pH 2 by adding 1NHCl with stirring under ice cooling, and extracted with chloroform. The solvent was evaporated under reduced pressure to obtain 2.60 g of a colorless oily product.

FAB mass spectrum m/z: 624 (M+H$^+$).

(2) N-Cyclopropylmethyl-Tyr-D-Arg-Phe-MeβAla-OH.diacetate

Boc-D-Arg($Z_2$)-Phe-MeβAla-OBzl (1.82 g, 2.10 mmol) was dissolved in 4NHCl/ethyl acetate solution (20 ml), and the solution was stirred at room temperature for 30 minutes. Diethyl ether was added to the reaction mixture, and the deposited crystal was collected by filtration. These crystals were dissolved in dimethylformamide (20 ml), and N-cyclopropylmethyl-N-benzyloxycarbonyl-Tyr(Bzl)-OH obtained in the above (1) (919 mg, 2.00 mmol), 1-hydroxybenzotriazole (297 mg, 2.20 mmol) and triethylamine (0.32 ml, 2.2 mmol) were dissolved in the solution. This solution was cooled to −10° C., then added with 1-ethyl-3-(3-dimethylaminopropyl)-carbodiimide hydrochloride (460 mg, 2.4 mmol), and stirred at −10° C. for one hour and then at room temperature for 20 hours. The reaction mixture was added with ethyl acetate (100 ml), and washed with 1NHCl and then with saturated aqueous sodium hydrogencarbonate. The solvent was concentrated under reduced pressure to obtain an oily product, which was purified by silica gel column chromatography (chloroform: methanol=100:1 (v/v)) to obtain 2.27 g of N-cyclopropylmethyl condensate as a colorless oily product.

The above protected peptide (1.24 g, 1.00 mmol) was dissolved in anhydrous hydrogen fluoride (5 ml) and anisole (1 ml), and the mixture was stirred with ice cooling for one hour. The reaction mixture was concentrated under reduced pressure. The residue was washed with ethyl acetate and then with diethyl ether, dissolved in water (5 ml), and then charged onto ion exchange resin (Diaion PA-308 acetate, 100 ml) and eluted with water. Fractions containing the desired compound was collected, and the solvent was evaporated under reduced pressure. Acetate of the resulting crude product was charged onto an ODS chromatography column (Fuji Silysia DM1020T, 50 g), and eluted stepwise with a gradient of 4–5% acetonitrile/0.1 N acetic acid solution. Fractions containing the desired compound were collected, and lyophilized to obtain 33 mg of the title compound as white powder.

FAB mass spectrum m/z: 624 (M+H$^+$); $[\alpha]_D^{23}$ +38.3° (c=1.05, 1N-acetic acid); Rf$^b$: 0.64.

EXAMPLE 6

N-(2-Aminoethyl)-Tyr-D-Arg-Phe-Meβala-OH.diacetate (1) N-Benzyloxycarbonyl-N-(2-t-butoxycarbonylaminoethyl)-Tyr-OH Try(Bzl)-OMe hydrochloride (2.57 g, 8.00 mmol) was dissolved in methanol (15 ml), and Boc-glycinol (1.20 g, 7.50 mmol) and sodium cyanoborohydride (0.47 g, 7.50 mmol) were dissolved in the solution with stirring under ice cooling. This solution was stirred at room temperature for 17 hours, concentrated under reduced pressure, added with chloroform (50 ml), and washed with water. This chloroform solution was added with saturated aqueous sodium hydrogencarbonate (15 ml) and benzyloxycarbonyl chloride (0.96 ml, 6.00 mmol), and then vigorously stirred at room temperature for 1 hour and 30 minutes. The chloroform layer was concentrated, and the resulting crude product was dissolved in methanol (20 ml), added with 2N aqueous sodium hydroxide (2.1 ml), and then stirred at room temperature for 11 hours. After the solvent was evaporated under reduced pressure, the mixture was adjusted to about pH 2 by adding 1NHCl with stirring under ice cooling, and extracted with ethyl acetate. The solvent was evaporated under reduced pressure to obtain 1.66 g of a colorless oily product.

FAB mass spectrum mlz: 613 (M+H$^+$), (2) N-(2-Aaminoethyl)-Tyr-D-Arg-Phe-Meβala-OH.diacetate By using Boc-D-Arg(Z$_2$)-Phe-MeβAla-OBzl (1.73 g, 2.00 mmol), N-benzyloxycarbonyl-N-(2-t-butoxycarbonylaminoethyl)-Tyr-OH obtained in the above (1) (1.10 g, 2.00 mmol), 1-hydroxybenzotriazole (270 mg, 2.00 mmol), triethylamine (0.28 ml, 2.0 mmol) and 1-ethyl-3-(3-dimethylaminopropyl)carbodiimide hydrochloride (479 mg, 2.5 mmol), the desired compound was obtained as in Example 1. The product was charged onto an ODS chromatography column (Fuji Silysia DM1020T, 50 g), and eluted stepwise using a gradient of 1–10% acetonitrile/0.1N acetic acid solution. Fractions containing the desired compound were collected, and lyophilized to obtain 259 mg of the title compound as white powder.

FAB mass spectrum m/z: 613 (M+H$^+$); $[\alpha]_D^{23}$ +36.80 (c=0.96, 1N-acetic acid); Rf$^b$: 0.51.

EXAMPLE 7

H-Gly-Tyr-D-Arg-Phe-MeβAla-OH.diacetate

By using Boc-Tyr(Bzl)-D-Arg(Z$_2$)-Phe-MeβAla-OBzl (3.35 g, 3.00 mmol), Boc-Gly-OH (0.52 g, 3.00 mmol), 1-hydroxybenzotriazole (405 mg, 3.00 mmol), triethylamine (0.42 ml, 3.0 mmol), and 1-ethyl-3-(3-dimethylaminopropyl)carbodiimide hydrochloride (690 mg, 3.60 mmol), a protected peptide Boc-Gly-Tyr(Bzl)-D-Arg (Z$_2$)Phe-MeβAla-OBzl (2.92 g) was obtained as in Example 1, and 741 mg (0.63 mmol) of the product was deprotected to obtain 370 mg of the desired compound as white powder.

FAB mass spectrum m/z: 627 (M+H$^+$); $[\alpha]_D^{23}$ +31.5 (c=1.00, 1N-acetic acid); Rf$^b$: 0.58.

EXAMPLE 8

N-Carboxymethyl-Tyr-D-Arg-Phe-MeβAla-OH (1) N-t-Butoxycarbonylmethyl-Tyr(Bzl)-OMe H-Try(Bzl)-OMe hydrochloride (16.1 g, 50.0 mmol) and t-butyl bromoacetate (19.5 g, 100 mmol) were dissolved in dimethylformamide (50 ml), and diisopropylethylamine (27 ml, 155 mmol) was added dropwise to this solution at room temperature over 20 minutes. After stirring at room temperature for 17 hours, insoluble substances were removed by filtration, and then the filtrate was concentrated under reduced pressure. The residue was dissolved in ethyl acetate (100 ml), and washed with 1NHCl and then with saturated aqueous sodium hydrogencarbonate. The solvent was concentrated under reduced pressure, and the residue was recrystallized from hexane to obtain 15.3 g of white crystals. Melting point: 66–67° C.

(2) N-Benzyloxycarbonyl-N-t-butoxycarbonylmethyl-Tyr(Bzl)-OH

N-t-Butoxycarbonylmethyl-Tyr(Bzl)-OMe obtained in the above (1) (2.00 g, 5.00 mmol) was dissolved in methylene chloride (20 ml), and the solution was added with 10% aqueous sodium carbonate (11 ml) and benzyloxycarbonyl chloride (0.96 ml, 6.00 mmol), and then stirred vigorously at room temperature for 2 hours and 30 minutes. The methylene chloride layer was concentrated, and the crude product was purified by silica gel column chromatography (benzene: ethyl acetate=30:1 (v/v)) to obtain a colorless oily product. This methyl ester was dissolved in methanol (40 ml), and the solution was added with 2N aqueous sodium hydroxide (20 ml), and then stirred at room temperature for seven hours. After the solvent was evaporated under reduced pressure, the reaction mixture was adjusted to about pH 2 by adding 1N HCl with stirring under ice cooling, and extracted with diethyl ether. The solvent was evaporated under reduced pressure to obtain 2.51 g of a colorless oily product.

FAB mass spectrum m/z: 520 (M+H$^+$).

(3) N-Carboxymethyl-Tyr-D-Arg-Phe-MeβAla-OH

By using Boc-D-Arg(Z$_2$)-Phe-MeβAla-OBzl (1.04 g, 1.20 mmol), N-benzyloxycarbonyl-N-t-butoxycarbonylmethyl-Tyr(Bzl)-OH obtained in the above (2) (624 mg, 1.20 mmol), 1-hydroxybenzotriazole (162 mg, 1.20 mmol), triethylamine (0.21 ml, 1.5 mmol), and 1-ethyl-3-(3-dimethylaminopropyl)carbodiimide hydrochloride (276 mg, 1.4 mmol), 187 mg of the title compound was obtained as white powder according to the method of Example 1.

FAB mass spectrum mlz: 628 (M+H$^+$); $[\alpha]_D^{23}$ +32.80 (c=0.98, 1N-acetic acid); Rf$^b$: 0.54.

EXAMPLE 9

N-Methanesulfonyl-Tyr-D-Arg-Phe-MeβAla-OH.diacetate

Boc-Tyr(Bzl)-D-Arg(Z$_2$)-Phe-MeβAla-OBzl (2.24 g, 2.00 mmol) was dissolved in 4N-HCl/ethyl acetate solution (15 ml), and the solution was stirred at room temperature for 30 minutes. Diethyl ether was added to the reaction mixture, and the deposited crystals were collected by filtration. These crystals were dissolved in dimethylformamide (5 ml), and the solution was added with diisopropylethylamine (0.5 ml), and further added with methanesulfonyl chloride (193 μl, 2.5 mmol)) with stirring under ice cooling. After stirring at room temperature for one hour, the reaction mixture was added with diethyl ether, and the insoluble substances were removed by filtration to obtain 1.13 g of N-methanesulfonyl-Tyr(Bzl)-D-Arg(Z$_2$)-Phe-MeβAla-OBzl.

This protected peptide (0.82 g, 0.75 mmol) was dissolved in acetic acid (5 ml), and added with 5% Pd-C (water content: 50%, 0.7 g) as catalyst, and catalytic reduction was carried out for 24 hours to remove the protective group.

After the catalyst was removed by filtration, the reaction mixture was lyophilized to obtain 400 mg of the title compound as white powder.

FAB mass spectrum m/z: 648 (M+H$^+$); $[\alpha]_D^{28}$ +20.40 (c=1.06, 1N-acetic acid); Rf$^b$: 0.67.

EXAMPLE 10

N-Formimidoyl-Tyr-D-Arg-Phe-MeβAla-OH.diacetate (1) N-Formimidoyl-N-benzyloxycarbonyl-Tyr(Bzl)-OH H-Tyr(Bzl)-OMe hydrochloride (6.43 g, 20.0 mmol) and isopropyl formimidate hydrochloride (8.24 g, 60.0 mmol) were dissolved in a mixture of dimethylformamide (15 ml) and methylene chloride (60 ml), and the solutinon was added with triethylamine (12 ml, 86 mmol) and stirred at room temperature for seven hours. After the insoluble substances were removed by filtration, the reaction mixture was added with saturated aqueous sodium hydrogencarbonate (50 ml) and benzyloxycarbonyl chloride (4.8 ml, 30.0 mmol), and then vigorously stirred at room temperature for 25 minutes. The methylene chloride layer was concentrated, and the resulting crude product was purified by silica gel column chromatography (chloroform: methanol=40:1 (v/v)) to obtain 3.45 g of a colorless oily product.

The resulting methyl ester (1.03 g, 2.31 mmol) was dissolved in a mixture of ethanol (10 ml) and dimethylformamide (5 ml), and the solution was added with 2N aqueous sodium hydroxide (2 ml) and stirred at room temperature for 2 hours and 30 minutes. After the solvent was evaporated under reduced pressure, the reaction mixture was adjusted to about pH 2 by adding 1N hydrochloric acid with stirring under ice cooling, and extracted with diethyl ether. The solvent was evaporated under reduced pressure to obtain 0.71 g of a colorless oily product.

FAB mass spectrum m/z: 433 (M+H$^+$).

(2) N-Formimidoyl-Tyr-D-Arg-Phe-MeβAla-OH.diacetate

By using Boc-D-Arg(Z$_2$)-Phe-MeβAla-OBzl (1.47 g, 1.70 mmol), N-for-mimidoyl-N-benzyloxycarbonyl-Tyr (Bzl)-OH obtained in the above (1) (650 mg, 1.50 mmol), 1-hydroxybenzotriazole (216 mg, 1.60 mmol), triethylamine (0.24 ml, 1.8 mmol) and 1-ethyl-3-(3-dimethylaminopropyl) carbodiimide hydrochloride (383 mg, 2.00 mmol), reaction was carried similarly to the method of Example 2. The resulting crude product was charged onto an ODS chromatography column (Fuji Silysia DM1020T, 50 g), and eluted stepwise by using a gradient of 3–15% acetonitrile/0.1N acetic acid solution. Fractions containing the desired compound were collected, and lyophilized to obtain 177 mg of the title compound as white powder.

FAB mass spectrum m/z: 597 (M+H$^+$); $[\alpha]_D^{23}$ +34.3 (c=1.00, 1N-acetic acid); Rf$^b$: 0.64.

EXAMPLE 11

N-Acetimidoyl-Tyr-D-Arg-Phe-MeβAla-OH.diacetate

H-Tyr-D-Arg-Phe-MeβAla-OH (690 mg, 1.00 mmol) and ethyl acetimidate hydrochloride (161 mg, 1.30 mmol) were dissolved in dimethylformamide (2 ml), and the solution was added with triethylamine (0.42 ml, 3.0 mmol) and then stirred at room temperature for two days. Diethyl ether (100 ml) was added to the reaction mixture, and the solvent was removed by decantation. The resulting crude product was charged onto an ODS chromatography column (Fuji Silysia DM1020T, 50 g), and eluted stepwise by using a gradient of 4–10% acetonitrile/0.1N acetic acid solution. Fractions containing the desired compound were collected, and lyophilized to obtain 388 mg of the title compound as white powder.

FAB mass spectrum m/z: 611 (M+H$^+$); $[\alpha]_D^{23}$ +23.1° (c=1.06, 1N-acetic acid); Rf$^b$: 0.58.

EXAMPLE 12

N-Propionimidoyl-Tyr-D-Arg-Phe-MeβAla-OH.diacetate

By using H-Tyr-D-Arg-Phe-MeβAla-OH (690 mg, 1.00 mmol), ethyl propionimidate hydrochloride (303 mg, 2.20 mmol) and triethylamine (0.56 ml, 4.0 mmol), reaction was carried out similarly to Example 11. The crude product was charged onto an ODS chromatography column (Fuji Silysia DM1020T, 25 g), and eluted stepwise by using a gradient of 0–10% acetonitrile/0.1N acetic acid solution. Fractions containing the desired compound were collected, and lyophilized to obtain 200 mg of the title compound as white powder.

FAB mass spectrum m/z: 625 (M+H$^+$); $[\alpha]_D^{23}$ +21.5° (c=1.0, 1N-acetic acid); Rf$^b$: 0.62.

EXAMPLE 13

N-Butylimidoyl-Tyr-D-Arg-Phe-MeβAla-OH.diacetate

By using H-Tyr-D-Arg-Phe-MeβAla-OH (510 mg, 0.76 mmol), ethyl butylimidate hydrochloride (256 mg, 1.66 mmol) and triethylamine (0.44 ml, 3.0 mmol), reaction was carried out similarly to Example 11. The crude product was charged onto an ODS chromatography column (Fuji Silysia DM1020T, 60 g), and eluted stepwise by using a gradient of 6–8% acetonitrile/0.1N acetic acid solution. Fractions containing the desired compound were collected, and lyophilized to obtain 173 mg of the title compound as white powder.

FAB mass spectrum m/z: 639 (M+H$^+$); $[\alpha]_D^{23}$ +17.00 (c=1.01, 1N-acetic acid); Rf$^b$: 0.63.

EXAMPLE 14

N-Benzimidoyl-Tyr-D-Arg-Phe-MeβAla-OH.diacetate

By using H-Tyr-D-Arg-Phe-MeβAla-OH (690 mg, 1.00 mmol), ethyl benzimidate hydrochloride (378 mg, 2.20 mmol) and triethylamine (0.56 ml, 4.0 mmol), reaction was carried out similarly to Example 11. The crude product was charged onto an ODS chromatography column (Fuji Silysia DM1020T, 25 g), and eluted stepwise by using a gradient of 0–14% acetonitrile/0.1N acetic acid solution. Fractions containing the desired compound were collected, and lyophilized to obtain 83 mg of the title compound as white powder.

FAB mass spectrum m/z: 673 (M+H$^+$); $[\alpha]_D^{23}$ +17.2° (c=1.0, 1N-acetic acid); Rf$^b$: 0.66.

EXAMPLE 15

N-[H$_2$NHNC(NH)]-Tyr-D-Arg-Phe-MeβAla-OH.diacetate (1) NC-Tyr(t-Bu)-D-Arg(Tos)-Phe-MeβAla-O-t-Bu Z-Phe-OH (29.9 g, 100 mmol), MeβAla-O-t-Bu (16.0 g, 110 mmol), and 3-hydroxy-4-oxo-3,4-dihydro-1,2,3-benzotriazine (17.9 g, 110 mmol) was dissolved in methylene chloride (200 ml). This solution was cooled to −10° C., added with 1-ethyl-3-(3-dimethylaminopropyl)carbodiimide hydrochloride (21.1 g, 110 mmol), and then stirred at −10° C. for one hour and further at room temperature for 20 hours. After the solvent was evaporated under reduced pressure, the reaction mixture was added with ethyl acetate (100 ml), and washed with 1N hydrochloric acid and then with saturated aqueous sodium hydrogencarbonate. The solvent was concentrated under reduced pressure to obtain an oily product, which was purified by silica gel column chromatography (benzene: ethyl acetate=10:1 (v/v)) to obtain 42.6 g of Z-Phe-MeβAla-O-t-Bu as a colorless oily product.

(2) Z-Phe-MeβAla-O-t-Bu (21.0 g, 47.6 mmol) was dissolved in methanol (200 ml), and added with 5% Pd-C (water content: 50%, 21 g) as catalyst, and catalytic reduction was carried out for four hours to remove the protective group. After the catalyst was removed by filtration, the solvent was evaporated under reduced pressure, and the residue was dissolved in dimethylformamide (100 ml). Z-D-Arg(Tos)-OH (20.0 g, 43.2 mmol) and 1-hydroxybenzotriazole (6.43 g, 47.6 mmol) were dissolved in the solution. The solution was cooled to −1° C., added with 1-ethyl-3-(3-dimethylaminopropyl)-carbodiimide hydrochloride (9.12 g, 47.6 mmol), and then stirred at −10° C. for one hour and further at room temperature for 18 hours. After the solvent was evaporated under reduced pressure, the reaction mixture was added with ethyl acetate (100 ml), and washed with 1N hydrochloric acid and then with saturated aqueous sodium hydrogencarbonate. The solvent was concentrated under reduced pressure to obtain 31.9 g of Z-D-Arg(Tos)-Phe-MeβAla-O-t-Bu as a colorless oily product.

(3) Z-D-Arg(Tos)-Phe-MeβAla-O-t-Bu (31.9 g, 41.0 mmol) was dissolved in methanol (200 ml), and added with 5% Pd-C (water content: 50%, 32 g) as catalyst, and catalytic reduction was carried out for four hours to remove the protective group. After the catalyst was removed by filtration, the solvent was evaporated under reduced pressure, and then the residue was dissolved in dimethylformamide (100 ml). Z-Tyr(t-Bu)-OH (13.7 g, 36.9 mmol) and 1-hydroxybenzotriazole (5.54 g, 41.0 mmol) were dissolved in the solution. This solution was cooled to −10° C., added with 1-ethyl-3-(3-dimethylaminopropyl)carbodiimide hydrochloride (7.86 g, 41.0 mmol), and then stirred at −10° C. for one hour and further at room temperature for 20 hours. After the solvent was evaporated under reduced pressure, the reaction mixture was added with ethyl acetate (100 ml), and washed with 1N hydrochloric acid and then with saturated aqueous sodium hydrogencarbonate. The solvent was concentrated under reduced pressure to obtain an oily product, which was purified by silica gel column chromatography (chloroform: methanol=40:1 (v/v)) to obtain 27.8 g of Z-Tyr (t-Bu)-D-Arg(Tos)-Phe-MeβAla-O-t-Bu as white powder.

$[\alpha]_D^{23}$ +18.8° (c=1.01, ethanol)

(4) Z-Tyr(t-Bu)-D-Arg(Tos)-Phe-MeβAla-O-t-Bu (11.6 g, 12.0 mmol) was dissolved in ethanol (60 ml), and added with 5% Pd-C (water content: 50%, 6 g) as catalyst, and catalytic reduction was carried out for 3 hours and 30 minutes to remove the Z group. After the catalyst was removed by filtration, the solvent was evaporated under reduced pressure. The residue was added with benzene (50 ml) and concentrated under reduced pressure and the procedure was repeated to remove the residual ethanol. The resulting colorless residue was dissolved in dry tetrahydrofuran (100 ml), and the solution was added with cyanogen bromide (1.69 g, 14.4 mmol)/methylene chloride (15 ml) solution with stirring at room temperature, and further added with triethylamine (2.02 ml, 14.4 mmol). After stirring at room temperature for 40 minutes, the deposited insoluble substances were removed by filtration. The filtrate was concentrated under reduced pressure to obtain an oily product, which was purified by silica gel column chromatography (chloroform: methanol=40:1 (v/v)) to obtain 5.70 g of colorless amorphous solid.

FAB mass spectrum m/z: 862 (M+H$^+$).

(5) NC-Tyr(t-Bu)-D-Arg(Tos)-Phe-MeβAla-O-t-Bu (1.00 g, 1.16 mmol) was dissolved in ethanol (5 ml), and the solution was added with hydrazine hydrochloride (158 mg, 2.3 mmol), and further added with triethylamine (0.42 ml, 3.0 mmol). After stirring at room temperature for three hours, the solvent was evaporated under reduced pressure. The residue was added with benzene (50 ml) and concentrated under reduced pressure and the procedure was repeated to remove the residual ethanol. The resulting residue was dissolved in 4N HCl/dioxane solution (10 ml), and the solution was stirred at room temperature for three hours, and then the solvent was evaporated under reduced pressure. Diethyl ether was added to the residue, and the deposited crystals were collected by filtration.

These crystals were dissolved in anhydrous hydrogen fluoride (10 ml) and anisole (1 ml), and the solution was stirred with ice cooling for one hour. The reaction mixture was concentrated under reduced pressure, and the residue was washed with ethyl acetate and then with diethyl ether, and dissolved in water (100 ml). The solution was charged onto an ion exchange resin (Daiaion PA-308 acetate, 100 ml), and then eluted with water. Fractions containing the desired compound were collected, and the solvent was concentrated under reduced pressure. Acetate of the resulting crude product was charged onto an ODS chromatography column (Fuji Silysia DM1020T, 25 g), and eluted stepwise by using a gradient of 2–10% acetonitrile/0.1N acetic acid solution. Fractions containing the desired compound were collected, and lyophilized to obtain 48 mg of the title compound as white powder.

FAB mass spectrum mlz: 628 (M+H$^+$); $[\alpha]_D^{20}$ +25.28 (c=0.720, 1N acetic acid); Rf$^a$: 0.25; Rf$^b$: 0.65.

EXAMPLE 16

N-[HOHNC(NH)]-Tyr-D-Arg-Phe-MeβAla-OH.diacetate

By using NC-Tyr(t-Bu)-D-Arg(Tos)-Phe-MeβAla-O-t-Bu (1.00 g, 1.16 mmol) and hydroxyamine hydrochloride (347 mg, 5.0 mmol), 288 mg of the title compound was obtained as white power as in Example 15.

FAB mass spectrum mlz: 629 (M+H$^+$); $[\alpha]_D^{20}$ +20.73 (c=0.965, 1N acetic acid); Rf$^a$: 0.38; Rf$^b$: 0.69.

EXAMPLE 17

N-(2-Imidazolyl)-Tyr-D-Arg-Phe-MeβAla-OH.monoacetate

H-Tyr-D-Arg-Phe-MeβAla-OH (400 mg, 0.58 mmol), 2-methylthio-2-imidazoline hydriodate (354 mg, 1.45 mmol) and triethylamine (0.28 ml, 2.0 mmol) were dissolved in dimethylformamide (20 ml), and the solution was stirred at 60° C. for 24 hours. Diethyl ether (100 ml) was added to the reaction mixture, and the solvent was removed by decantation. The resulting oily product was charged onto an ODS chromatography column (Fuji Silysia DM1020T, 50 g), and eluted stepwise by using a gradient of 3–13% acetonitrile/0.1N acetic acid solution. Fractions containing the desired compound were collected, and lyophilized to obtain 14 mg of the title compound as white powder.

FAB mass spectrum mlz: 639 (M+H$^+$); $[\alpha]_D^{20}$ +11.14 (c=0.700, 1N acetic acid); Rf$^a$: 0.25; Rf$^b$: 0.65.

EXAMPLE 18

N-[2-(4,6-Dimethyl)pyrimidyl]-Tyr-D-Arg-Phe-MeβAla-OH (1) Boc-Phe-OH and TosOH MeβAla-OBzl were condensed by the EDC-HOBt method to obtain Boc-Phe-MeβAla-Obzl. Boc group was removed from the Boc-Phe-MeβAla-OBzl by using 4N HCl/ethyl acetate ester, and the resultant was condensed with Boc-D-Arg(Z$_2$)-OH by the EDC-HOBt method to obtain Boc-D-Arg(Z$_2$)-Phe-MeβAla-OBzl. Subsequently, Boc group was removed from the Boc-D-Arg(Z$_2$)-Phe-MeβAla-OBzl by using 4N HCl/ethyl acetate ester, and the resultant was condensed with Boc-Tyr (Bzl)-OH by the EDC-HOBt method to obtain a protected peptide BocTyr(Bzl)-D-Arg(Z$_2$)-Phe-MeβAla-OBzl.

Boc-Tyr(Bzl)-D-Arg(Z$_2$)-Phe-MeβAla-OBzl (3.32 g, 3.00 mmol) was dissolved in 4N HCl/ethyl acetate solution (10 ml), and the solution was stirred at room temperature for 40 minutes. Diethyl ether was added to the reaction mixture, and the deposited crystals were collected by filtration. These crystals were dissolved in dimethylformamide (10 ml), and the solution was added with triethylamine (1.68 ml, 12 mmol), N,N'-bis-t-butoxycarbonylthiourea (229 mg, 3.00 mmol) and silver chloride (I) (896 mg, 3.3 mmol) with stirring under ice cooling, and then the mixture was stirred at room temperature for 20 minutes. Ethyl acetate (100 ml) was added to the reaction mixture, and the deposited insoluble substances were removed by filtration. The filtrate was washed with water and concentrated under reduced pressure to obtain an oily product, which was purified by silica gel column chromatography (chloroform: methanol= 40:1 (v/v)) to obtain 2.54 g of Boc-HNC-(N-BOc)-Tyr(Bzl)-D-Arg($Z_2$)-Phe-MeβAla-OBzl as colorless amorphous solid.

(2) The Boc-HNC(N-Boc)-Tyr(Bzl)-D-Arg($Z_2$)-Phe-MeβAla-OBzl (1.25 g, 1.00 mmol) obtained in the above (1) was dissolved in 4N HCl/ethyl acetate solution (10 ml), and stirred at room temperature for 2 hours and 30 minutes. Diethyl ether was added to the reaction mixture, and the deposited crystals were collected by filtration. These crystals were dissolved in dimethylformamide (10 ml), and the solution was added with triethylamine (0.2 ml, 1.4 mmol), 2,4-pentanedione (1.05 ml, 10.0 mmol) and 1% sodium carbonate (6 ml) with stirring under ice cooling, and then stirred at room temperature for ten days. Water (40 ml) was added to the reaction mixture, and the deposited solid was collected by filtration. The resulting solid was purified by silica gel column chromatography (chloroform: methanol= 100:1 (v/v)) to obtain 0.55 g of 2-(4,6-dimethyl)pyrimidyl-Tyr(Bzl)-D-Arg(Z)-Phe-MeβAla-OBzl as colorless amorphous solid.

(3) The compound obtained in the above (2) (477 mg, 0.43 mmol) was dissolved in methanol (20 ml), and the solution was added with 5% Pd-C (water content: 50%, 0.3 g) as catalyst, and catalytic reduction was carried out for six hours. After the catalyst was removed by filtration, the solvent was evaporated under reduced pressure, and the residue was dissolved in water (50 ml), and lyophilized to obtain 259 mg of the title compound as white powder.

FAB mass spectrum mlz: 663 (M+H$^+$); $[\alpha]_D^{20}$ +11.84 (c=0.999, 1N acetic acid); Rf$^a$: 0.58; Rf$^b$: 0.73.

TEST EXAMPLE

The analgesic activities of peptide derivatives of the present invention were evaluated by pressure stimulation method as follows. Mice were subjected to pressure stimulation at the bases of their tails at a rate of 10 mmHg/second. Pressure values where the mice showed behaviors such as writhing and biting at the stimulated site were measured and were used as pain reaction thresholds. For the experiments, mice that were preliminary determined to respond to a pressure of 40–50 mmHg were used. The maximum stimulating pressure was 100 mmHg. Analgesic activity was calculated as percent of maximum possible effect (% of MPE) according to the following equation:

$$\% \text{ of } MPE = \frac{Pt - Po}{Pc - Po} \times 100$$

wherein Po is the pain reaction threshold before the administration of a drug; Pt is the pain reaction threshold "t" minutes after the administration of the drug; and Pc is the maximum stimulating pressure. According to a dose-response curve, ED$_{50}$ value was determined as a dose of drug providing 50% of % of MEP and used for comparison of analgesic activity of drugs.

The compound of Example 11 was examined by subcutaneous administration (skin in the backs) and oral administration, and it was found that ED$_{50}$ values were 0.098 mg/kg and 2.65 mg/kg, respectively. ED$_{50}$ values (mg/kg) of morphine used as control were 4.6 mg/kg and 29.6 mg/kg for subcutaneous administration (back subcutis) and oral administration, respectively.

INDUSTRIAL APPLICABILITY

The peptide derivatives of the present invention are useful since they can be used for the treatment of cancerous pain and the like.

What is claimed is:

1. A compound represented by the following formula, or a salt thereof: N-methyl-Tyr-D-Arg-Phe-N-methylβAla.

2. The salt of the compound of claim 1, wherein the salt comprises hydrochloride or acetate.

3. A medicament comprising the compound or salt of claim 1.

4. An analgesic pharmaceutical composition comprising as an active ingredient the compound or salt of claim 1.

5. A method for preventive and/or therapeutic treatment of pain comprising administering to a mammal a preventively or therapeutically effective amount of the compound or salt of claim 1.

* * * * *